(12) United States Patent
Maruccio

(10) Patent No.: US 8,271,071 B2
(45) Date of Patent: Sep. 18, 2012

(54) APPARATUS FOR SENSING AND PROCESSING ELECTRICAL CARDIAC SIGNALS AND METHOD OF REMOTE SENSING AND PROCESSING OF ELECTRICAL CARDIAC SIGNALS

(76) Inventor: Fabiana Salles Maruccio, São Paulo (BR)

( * ) Notice: Subject to any disclaimer, the term of this patent is extended or adjusted under 35 U.S.C. 154(b) by 1078 days.

(21) Appl. No.: 12/220,654

(22) Filed: Jul. 25, 2008

(65) Prior Publication Data

US 2009/0182241 A1    Jul. 16, 2009

Related U.S. Application Data

(63) Continuation of application No. PCT/BR2007/000014, filed on Jan. 25, 2007.

(30) Foreign Application Priority Data

Jan. 25, 2006  (BR) ..................... 0603508

(51) Int. Cl.
*A61B 5/0402*    (2006.01)
(52) U.S. Cl. ......... 600/509; 600/515; 600/523; 128/903
(58) Field of Classification Search .......... 600/508–509, 600/515, 523; 128/923
See application file for complete search history.

(56) References Cited

U.S. PATENT DOCUMENTS

| 4,295,472 A | 10/1981 | Adams |
| 2002/0045836 A1 | 4/2002 | Alkawwas |

FOREIGN PATENT DOCUMENTS

| WO | WO 99/60919 | 12/1999 |
| WO | WO 02/089667 | 11/2002 |

OTHER PUBLICATIONS

International Search Report for Application No. PCT/BR2007/000014, dated May 9, 2007.

*Primary Examiner* — Carl H Layno
*Assistant Examiner* — Deborah Malamud
(74) *Attorney, Agent, or Firm* — TraskBritt

(57) ABSTRACT

Described is an apparatus for sensing and processing electrical cardiac signals in a user's body, the apparatus comprising a contact surface having a plurality of electrical signal sensing electrodes associated with an electronic processing circuit and communication unit. The apparatus is configured for sensing electrical signals and is arranged within a single housing. It is configured to perform complete ECG bipolar, unipolar and unipolar precordial leads by at least four associations of the apparatus with the subject's skin. Also described is a method of remote sensing and processing of electrical cardiac signals which, via the apparatus, enables a lay user, or even the patient, to obtain the patient's heart signals.

6 Claims, 5 Drawing Sheets

APPARATUS FOR SENSING AND PROCESSING ELECTRICAL CARDIAC SIGNALS AND METHOD OF REMOTE SENSING AND PROCESSING OF ELECTRICAL CARDIAC SIGNALS

CROSS-REFERENCE TO RELATED APPLICATIONS

This application is a continuation of International Patent Application No. PCT/BR2007/000014, filed Jan. 25, 2007, designating the United States of America, and published, in English, as PCT International Publication No. WO 2007/085068 A1 on Aug. 2, 2007, which application claims priority to Brazilian Application No. PI0603508-6, filed Jan. 25, 2006, the entire contents of each of which are hereby incorporated herein by this reference.

TECHNICAL FIELD

The present invention relates to an apparatus for sensing and processing electrical cardiac signals for ECG, enabling its use by lay users because of simple and compact design, and to a method of remote sensing and processing of electrical cardiac signals which, by means of said apparatus for sensing and processing cardiac signals, enables a lay user to obtain his/her own heart signals or those of other persons and send them to a remote processing unit ready for generating the ECG graph.

BACKGROUND

Different types of electrocardiographs and cardiac monitors are known in the art and, in this sense, a great deal of work has been developed to simplify these pieces of equipment without losing the accuracy and reliability of the signals obtained and processed.

It is known that electrocardiographs are devices that detect electrical signals associated with the activity of the heart in order to produce electrocardiograms (ECG), which basically consist of a graphical record of the electrical voltage as a function of time. Therefore, an ECG consists of a non-invasive medical diagnostic method widely used in the follow-up of cardiac pathologies and routine examinations.

The first enhancements to the electrocardiographs date from 1872, and currently a great deal of effort is put into the development of increasingly simpler, portable and personal pieces of equipment enabling their use by the users/patients themselves outside the hospital environment.

Typically, the record of the heart's electrical activity is made through electrodes or sensors placed on specific points of the user's body surface. These electrodes sense the sequences of electrical events occurring in the cardiac cycle (systoles and diastoles) and which propagate to the body surface, these events later being processed and extracted into ECG graphs.

For sensing these electrical cardiac signals, predetermined points are respected on which said electrodes should be positioned. This distribution of electrodes at predetermined points is known as lead, and usual leads are bipolar leads, unipolar leads and unipolar precordial leads. For each type of lead, a certain number of electrodes is used and arranged on different positions. Thus, traditional electrocardiographs formed by wires with sensors or electrodes at one of their ends are widely used, these electrodes being positioned on the user in the following manner: two electrodes on the arm, one electrode on the left leg and six electrodes distributed on the thoracic region. A simpler variation of this traditional method uses three wires with electrodes on one of the ends and two or four more electrodes (depending on the model) housed on the surface of the apparatus.

Because of the excessive quantity of wires used in traditional electrocardiographs, two color codes have been assigned in an attempt to standardize and simplify the handling of these wires. In the first code, the following colors are used: red, green and yellow, and handling should be done as follows: green on the waist region of the patient's left side; red on the right hand, wrist and axilla; yellow on the left hand, wrist and axilla. In the second code, the following colors are used: white, black and red, and handling should be done as follows: red on the waist region of the patient's left side; white on the right hand, wrist or axilla and black on the left hand, wrist or axilla. With regard to the sensors on the surface of the apparatus, they are positioned on the patient's thorax in three positions that vary from the center of the thorax to the left lateral region, next to the ribs.

An inconvenience presented by these traditional electrocardiographs consists of the large amount of color-coded wires used, requiring a trained professional skilled in performing the examination, thus avoiding the use of these pieces of equipment by lay users. This becomes a problem in the case of an emergency wherein the patient to be treated is not in a hospital environment, for instance, in case the patient has cardiac complications at home, these devices cannot be used by those accompanying the patient to identify the reasons for his/her indisposition. This leads to the need for urgent removal of the patient to a hospital and a relative delay until the heart problem is actually detected and confirmed.

Another disadvantage is in the lower durability of the wires in relation to the other components of the equipment, requiring extra handling. Furthermore, the inadequate handling of the wires increases the incidences of noise and interference in the sensing of the signal, which may affect the quality of the data sensed as well as the ECG graph obtained.

In order to solve this problem, document US 2002/0045836 discloses multiple wireless sensor assemblies for individually attachment to standard body locations for ECG signal recording. This system does not use wires once the electrodes are comprised within an housing with an integrated circuit and a wireless transmitting device. Nevertheless, this system needs at least two housings with electrodes in order to obtain a complete ECG bipolar, unipolar or unipolar precordial measurement. Additionally, several placements of the housings are required. This results in difficult handling and a non intuitive method, requiring a trained professional skilled in performing cardiac examination.

The document WO 02/089667 also discloses an apparatus for monitoring an electrical signal from a patient's body including a disposable patch with a plurality of electrodes, a converter, a processor and a transmitter for transmitting the processed digital signal as wireless signal. This system can monitor different electrical impulses by various organs by placing the disposable electrode patches on the selected organ. One of the possible measurements is an electrocardiogram. However, this document only describes that it can do electrocardiogram measurements, but it does it does not describe that the electrode patch can perform a complete (twelve leads) electrocardiogram measurement by different positioning of one electrode patch.

OBJECTS OF THE INVENTION

The present invention has as its object to provide a compact and simple apparatus for sensing and processing electrical cardiac signals, which can be used by lay users/patients, enabling the sensing of electrical cardiac signals and the selective transformation thereof into several existing leads (bipolar, unipolar and unipolar precordial) in order to obtain ECG graphs. Therefore, a user or patient is able to sense his/her own electrical cardiac signals at the smallest sign of alteration or discomfort and transform them into the pertinent leads to be later transmitted to the hospital environment where, in a fast and effective way, an ECG graph is generated, avoiding major health complications to this patient.

It is a further object of this invention to provide a method of remote sensing and processing of the electrical cardiac signals which, by means of said apparatus for sensing and processing electrical cardiac signals, enables the sensing and transformation of electrical signals, as well as their transmission to remote processing units to generate ECG graphs.

BRIEF SUMMARY OF THE INVENTION

The invention has as its object an apparatus for sensing and processing electrical cardiac signals in human body of a user comprising a contact surface, said contact surface comprising a plurality of electrical signal sensing electrodes associated with an electronic processing circuit and communication means, the apparatus having:

(i) the electrodes for sensing electrical signals, the electronic processing circuit and the communication means are arranged inside a single housing;

(ii) a single of said apparatus performs complete ECG bipolar, unipolar and unipolar precordial leads by at least four associations of the apparatus with the user's skin at a thoracic or abdominal region wherein at least one electrode for sensing electrical signals is contactable by a finger of the user when the apparatus is in association with the users body;

(iii) said electrical signals sensed from the heart being processed by the electronic processing circuit in order to selectively transform said electrical signals into the ECG bipolar, unipolar and unipolar precordial leads; and (iv) the ECG bipolar, unipolar and unipolar precordial leads information being wireless sent to a remote processing unit to generate the ECG graphs.

A further object of the invention is a method of remote sensing and processing of electrical cardiac signals of a human body by means of an apparatus for sensing and processing electrical cardiac signals, said apparatus comprising a plurality of electrical signal sensing electrodes associated with an electronic processing circuit, said method being characterized in that it comprises the steps of:

A) Obtaining the three classical leads DI, DII and DIII and the three augmented leads aVF, aVR and aVL with a single positioning of the apparatus associated with a body surface of a frontal portion of a user's skin at a thoracic or abdominal region so that an electrode, arranged on a single housing of the apparatus is directed to a user's left leg and, simultaneously, contacting a first finger of the user's hand on another electrode and a second finger of the user's hand on still other electrode, said first and second fingers originating from different hands of the same user;

B) Positioning the housing of the apparatus on three different standard body locations of the user's thoracic region for the precordial sensing;

C) Sensing of electrical signals originating from the user's heart for each of the standard body locations of steps A and B and transmitting these signals to the electronic processing circuit;

D) Processing the electrical signals sensed by the electrical signal sensing electrodes by the electronic processing circuit and selectively transforming these electrical signals into ECG bipolar, unipolar or unipolar precordial leads; and E) Transmitting wirelessly the twelve ECG bipolar, unipolar or unipolar precordial leads to at least one processing unit, the processing unit transforming the leads into ECG graphs.

BRIEF DESCRIPTION OF DRAWINGS

The present invention will be further described in more details based on one example of execution represented in the drawings. The figures show.

DETAILED DESCRIPTION OF DRAWINGS

Figure 1:
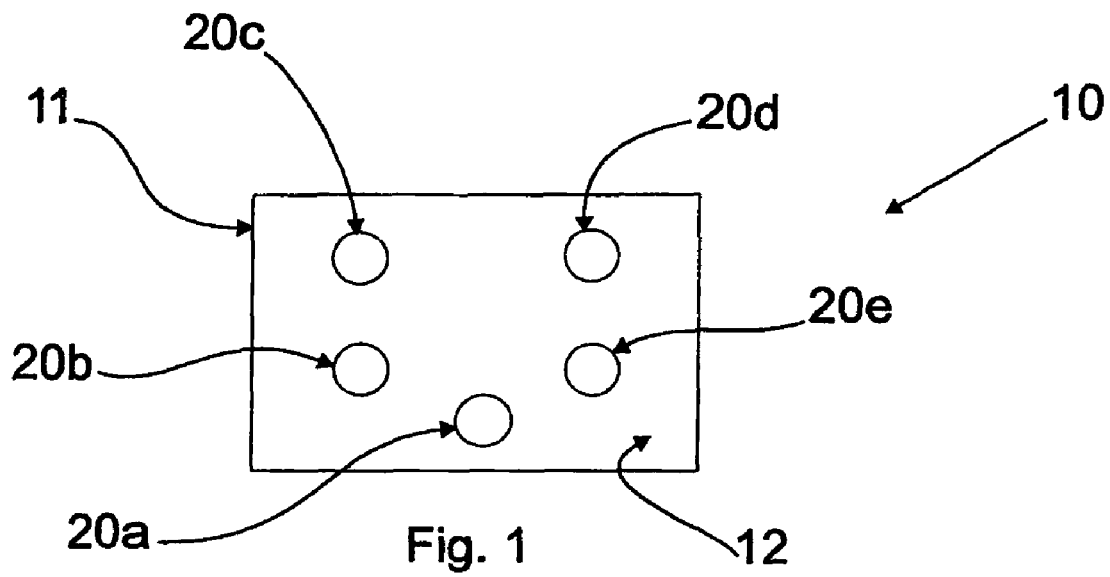
FIG. 1 is a schematic view of the apparatus for sensing and processing electrical cardiac signals object of this invention.

According to a preferable embodiment, and as can be seen in FIG. 1, apparatus 10 for sensing and processing electrical cardiac signals comprises a plurality of electrodes for sensing electrical signals 20a, 20b, 20c, 20d, 20e, consecutively positioned on a contact surface 12 of a housing 11, in accordance with a determined sequence for sensing electrical signals. In particular, the arrangement of these electrodes is done clockwise, starting with a first electrode 20a following in order until a fifth electrode 20e; however, other different arrangements may be adopted, provided the apparatus 10 retains its functionality.

Figure 3:
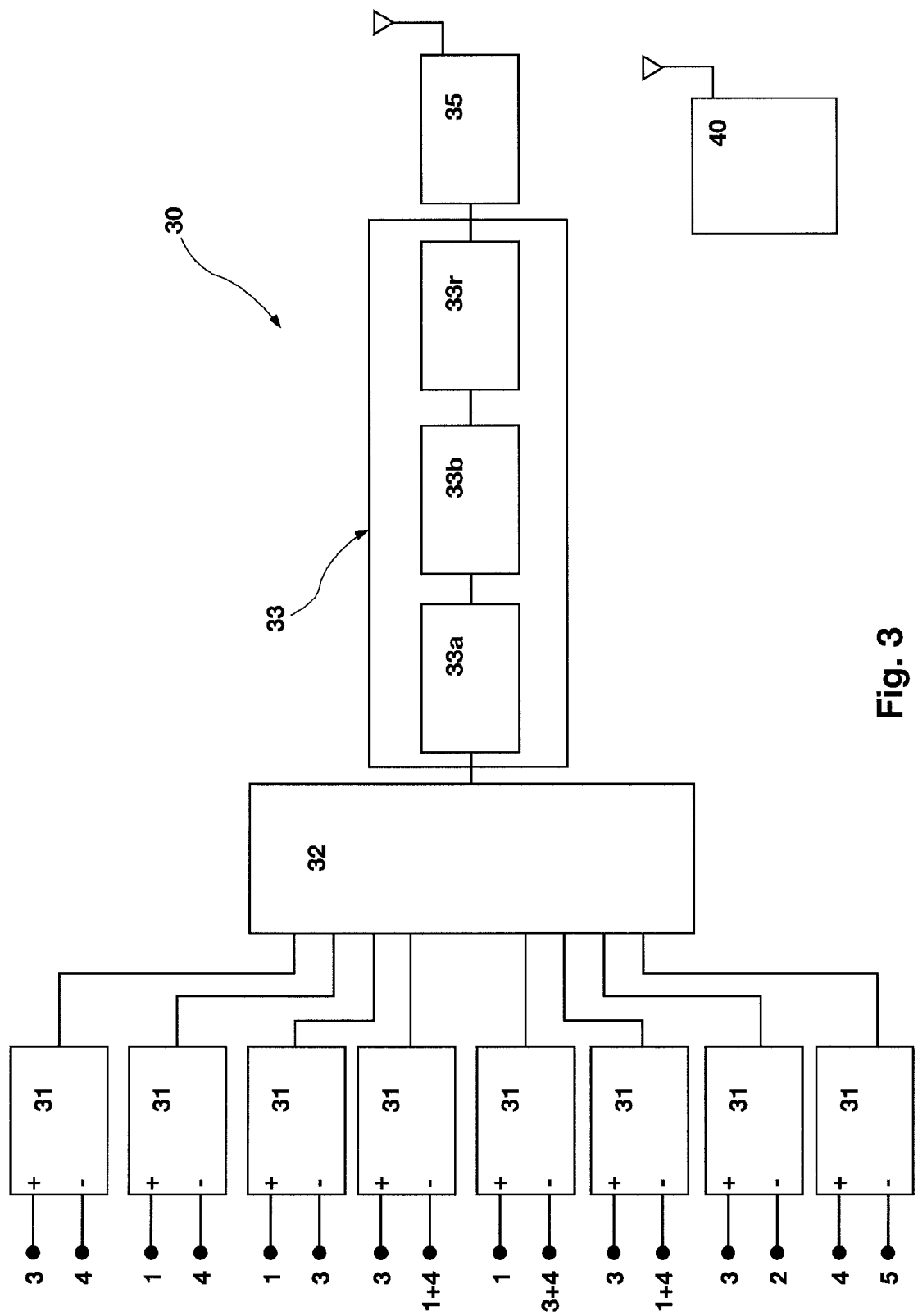
FIG. 3 is a block diagram illustrating the sensing and transformation of signals obtained by the apparatus for sensing and processing electrical cardiac signals object of this invention.
Figure 4A:
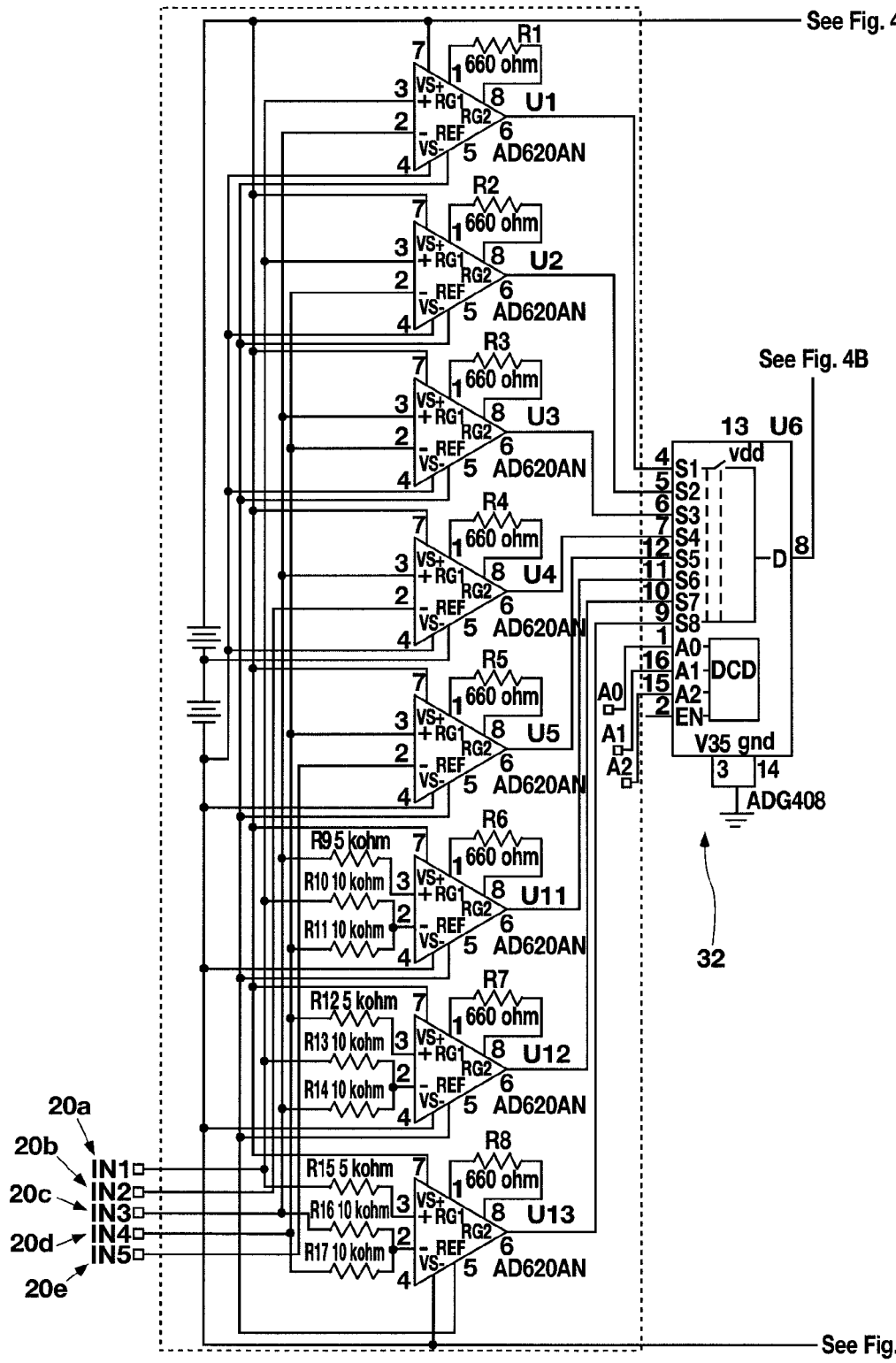
FIG. 4 is an electronic schematic view of the electronic processing circuit that comprises the apparatus for sensing and processing electrical cardiac signals object of this invention.
Figure 4B:
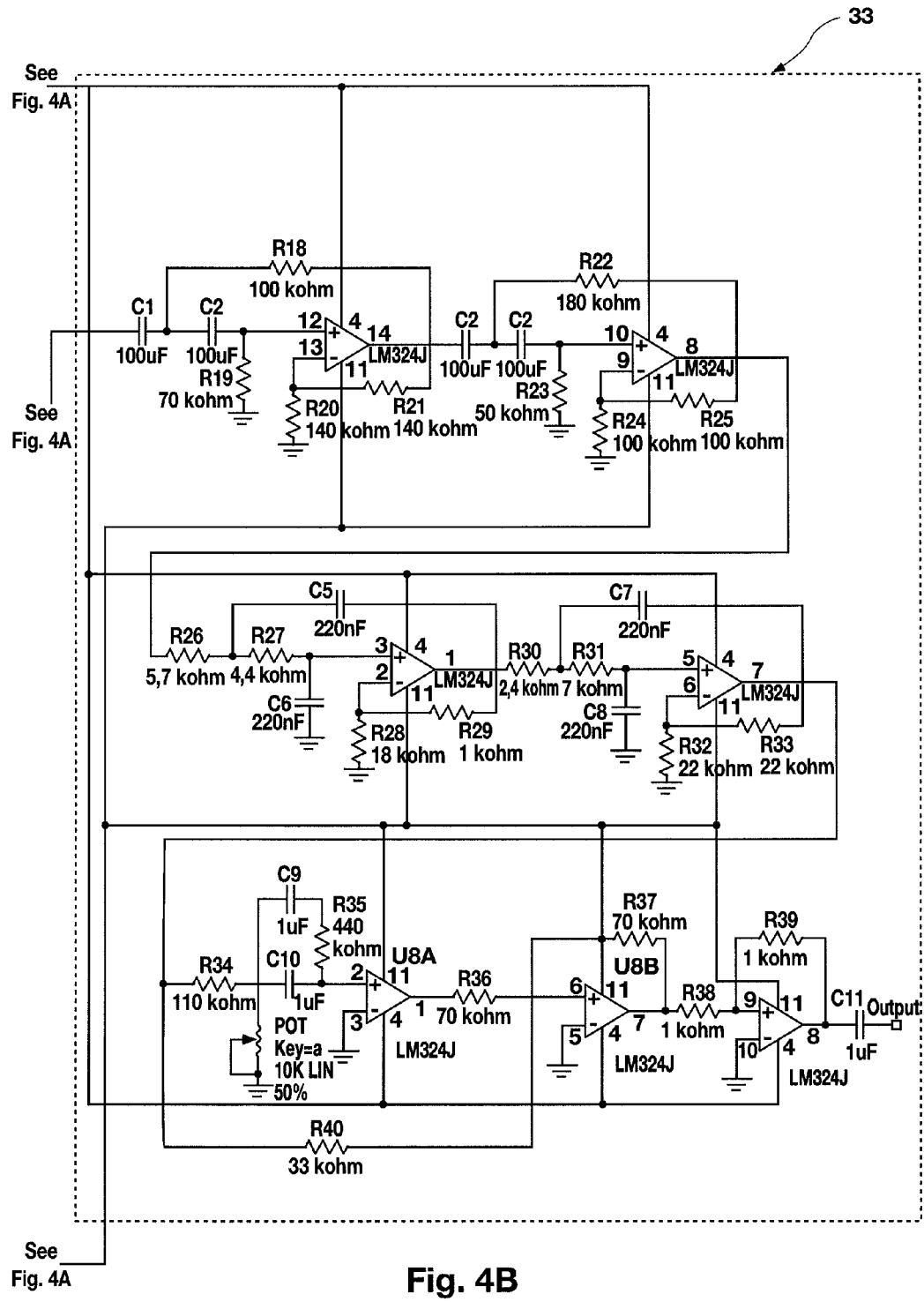
Figure 5:
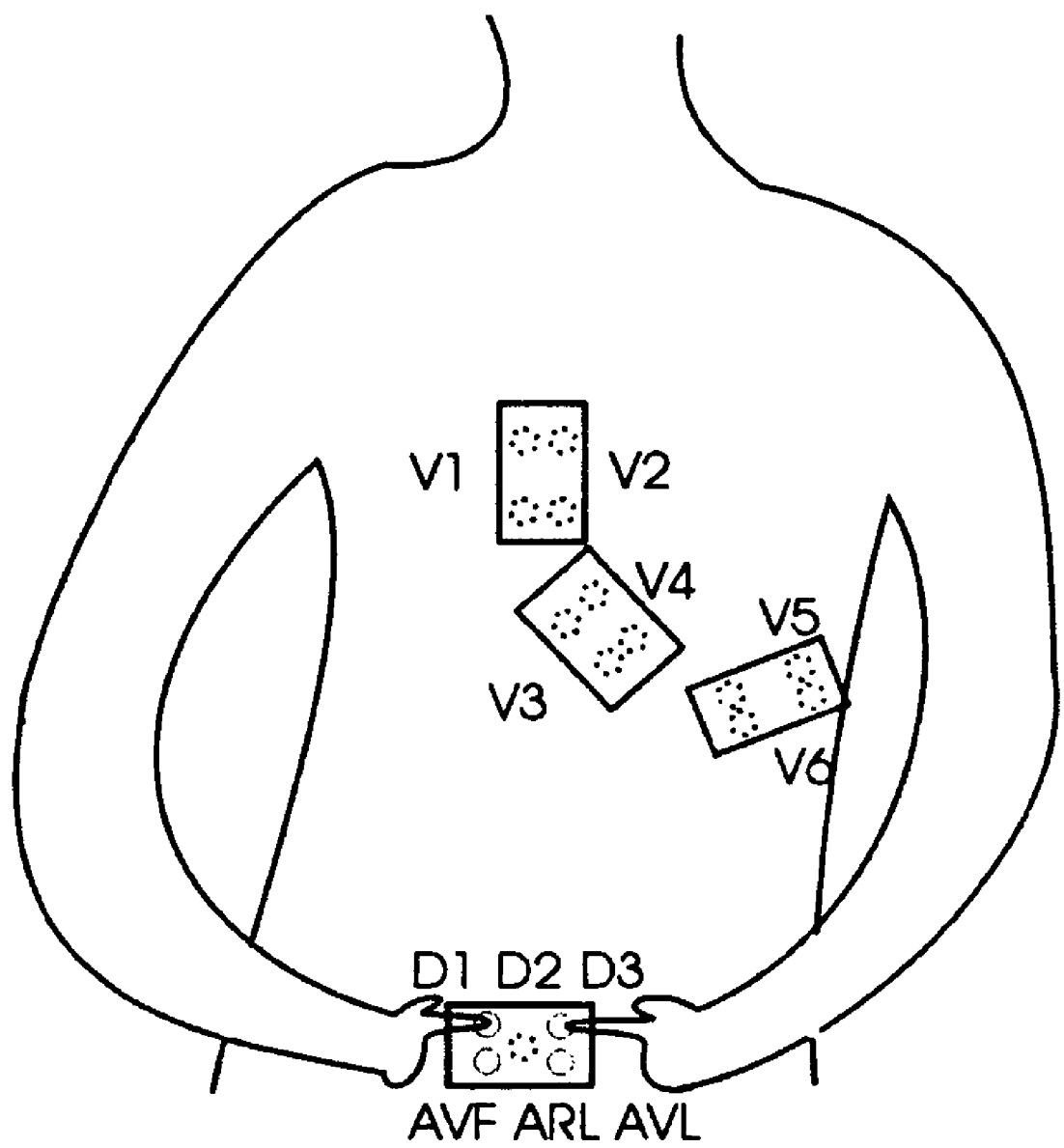
FIG. 5 is a schematic view of the positioning of the apparatus for sensing and processing electrical cardiac signals illustrated in FIG. 1

The electrodes for sensing electrical signals 20a, 20b, 20c, 20d, 20e are associated with an electronic processing circuit 30, as illustrated in FIGS. 3 and 4.

This electronic processing circuit 30 comprises instrumentation amplifiers 31 (AD620), particularly used to measure analog signals of low amplitude originating from remote sources, since they are optimized to operate in situations wherein signal acquisition is difficult. Its function in this circuit is to define the needed leads. and, for the present invention, it has the following main characteristics:

Gain of up to $10^3$ with the change of only one resistor (Rg);

Symmetrical feed: 2.3V to 18V; and

CMRR: 73 to 130 dB.

The instrumentation amplifiers 31 are associated with the electrodes for sensing electrical signals 20a, 20b, 20c, 20d, 20e, in pairs and receive from them the sensed electrical cardiac signals. The instrumentation amplifiers 31 are also associated with a switching device 32, this switching device being an analog multiplex (ADG608), for instance, which by means of a binary code (digital command) makes the selection of a certain lead to be analyzed. The function of an analog multiplex is to make the distribution of channels along a frequency range and, for the present invention, this switching device 32 has preferably eight inputs and one output, the inputs being determined by three addressable bits.

Completing the electronic processing circuit 30, the switching device 32 is associated with a filter block 33. For low amplitude signals, active filters are used, hence, in the electronic processing circuit 30 of the present invention, the forth-order "Butterworth" topology is adopted, which works at low frequency and also confers a gain to the system. Therefore, this circuit 30 was implemented with three active filters 33a, 33b, 33r interconnected in cascade resulting in a filter block with a frequency range of 0.05 Hz to 150 Hz, rejecting the 60 Hz frequency, as illustrated in FIG. 3. The filters 33a, 33b, 33r used in the preferable embodiment of this invention are of the LM324 type, having four operational amplifiers integrated into a same silicon chip enabling the use of printed circuit board of small size. Therefore, the filter block 33 comprises a high pass filter 33a with a determined frequency of fc=0.05 Hz; a low pass filter 33b with a determined frequency of fc=150 Hz; and a band reject filter 33r with a determined frequency of fc=60 Hz.

The ECG signals sensed by the electrical signal sensing electrodes 20a, 20b, 20c, 20d, 20e and transformed by the electronic processing circuit 30 are received by the receiver of the sensed ECG signal 35 to be later sent to a processing unit 40.

FIG. 4 shows the scheme for sensing electrical cardiac signals containing 12 (twelve) leads.

It should be noted that the electrical signal sensing electrodes 20a, 20b, 20c, 20d, 20e and the electronic processing circuit 30 are arranged inside the housing 11 of the apparatus 10; however, the dimensions of said apparatus 10 are reduced, which makes it more practical and easy to handle and facilitates the use of its functions, which will be described in detail below.

Figure 2:
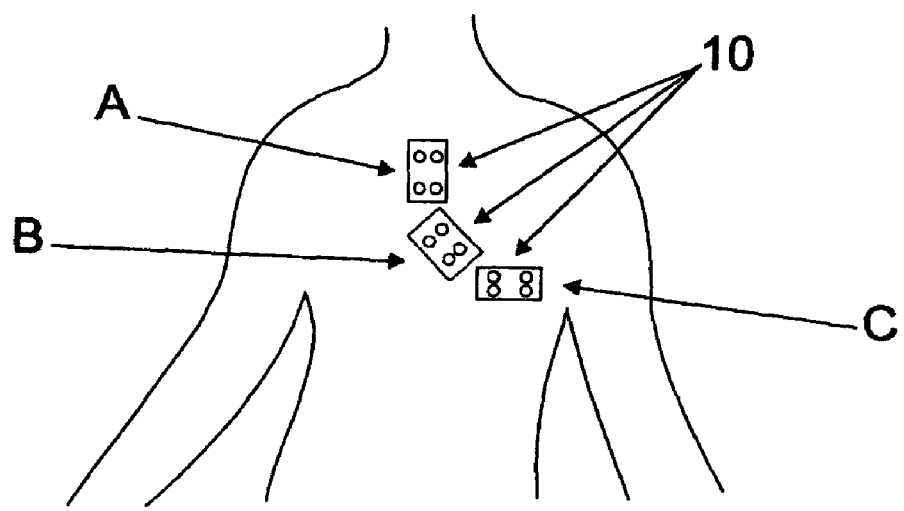
FIG. 2 is a schematic view of the positioning of the apparatus for sensing and processing electrical cardiac signals illustrated in FIG. 1.

The use of the apparatus 10 for sensing and processing electrical cardiac signals occurs with the association of the housing 11 of said apparatus 10 with body surfaces of frontal portions of users' anterior limbs, that is, by placing the contact surface 12 of the housing 11 in contact with the frontal portions of the users' anterior limbs, which consist of the user's thorax or abdomen, such as illustrated in FIG. 2. In addition, at least one and preferably two of the electrical signal sensing electrodes 20a, 20b, 20c, 20d, 20e are digitally contactable, by means of the contact of the user's fingers with these electrodes, as will be further described.

With this positioning of the housing 11 of the apparatus 10, the electrical cardiac signals sensed by the electrical signal sensing electrodes 20a, 20b, 20c, 20d, 20e are received and processed by an electronic processing circuit 30, so that the electrical signals are selectively transformed into ECG bipolar, unipolar or unipolar precordial leads. At the end of the processing and transformation, the electrical signals pass to a receiver of the sensed ECG signal 35 and are later transmitted to a processing unit 40 via communication protocols and telephone routes, through transmission means.

The present invention also relates to a method of remote sensing and processing of electrical cardiac signals which, by means of said apparatus 10 for sensing and processing electrical cardiac signals described above, enables to remotely obtain electrical cardiac signals of a user or patient, transform these signals into pertinent leads to prepare an ECG graph and send them to a processing unit 40, where they will be converted into ECG graphs. Therefore, this method comprises the steps of:

A) Positioning the apparatus 10 associated with a body surface of a frontal portion of a user's anterior limb so that a first electrical signal sensing electrode 20a, arranged on the housing 11 of the apparatus 10 is directed to a user's left leg and positioning a first finger of the user over a third electrode for sensing electrical signals 20c and a second finger of the user over a fourth electrode for sensing electrical signals 20d, said first and second fingers originating from different hands;

B) Sensing of electrical cardiac signals originating from the user's heart and transmitting these signals to the electronic processing circuit 30;

C) Processing the electrical cardiac signals sensed by the electrical signal sensing electrodes 20a, 20b, 20c, 20d, 20e and selectively transforming these electrical signals into ECG bipolar, unipolar or unipolar precordial leads; and D) Transmitting the ECG bipolar, unipolar or unipolar precordial leads to at least one processing unit 40.

In step A, the contact surface 12 of the housing 11 of the apparatus 10 for sensing and processing electrical signals is put into contact with the body surface of the user's thoracic region or abdomen.

The advantage provided by the apparatus 10 for sensing and processing electrical cardiac signals and by the method of remote sensing and processing electrical cardiac signals, which are the objects of the present invention, consists of enabling the obtainment of three classical leads DI, DII and DIII, as well as three augmented leads aVF, aVR and aVL, with only one positioning of the housing 11 of the apparatus 10 on a determined region of the patient's body.

Furthermore, although there is a need to place the housing 11 of the apparatus 10 for sensing and processing electrical cardiac signals in three different positions on the body surface of the user's thoracic region or abdomen to obtain the signals and transform them into the precordial leads, as shown in FIG. 2, still the practicality of said apparatus 10 and the easy obtainment of the desired leads with a lower number of positionings render it superior to similar apparatuses known in the art.

With regard to the positions illustrated in FIG. 2, with the housing 11 arranged on the first position A, two leads are acquired, such leads being V1 and V2; on the second position B, leads V3 and V4 are acquired and, finally, on the third position C, leads V5 and V6 are acquired.

Therefore, the positioning of the apparatus 10 for the desired sensing, regardless of the type of lead to be obtained, is done by placing the contact surface 12 of the housing 11 of the apparatus 10 associated, or in contact, with a body surface of a frontal portion of a user's anterior limb, more precisely in contact with the abdomen so that the first electrode for sensing electrical signals 20a is directed to the user's left leg. Then, the user places his/her left hand thumb over the third electrode for sensing electrical signals 20c and then places the right hand thumb 20c over the fourth electrode for sensing electrical signals 20d. The other fingers of the user's hands are positioned on an electrical ground point (no illustrated) of the apparatus 10.

Once the apparatus 10 is positioned, step B starts with the sensing of electrical signals from the user's heart, which is done according to a timing programmed by the electronic processing circuit 30, that is, by means of this timing it is possible to control the time in which each signal will be analyzed.

In step C, the processing of the electrical signals sensed by electrodes for sensing electrical signals 20a, 20b, 20c, 20d, 20e is done by the electronic processing circuit 30.

In this sense, and as already mentioned, the processing of the electrical signals sensed starts with the reception of the signals sensed by the electrodes for sensing electrical signals 20a, 20b, 20c, 20d, 20e and by the instrumentation amplifiers 31 that define the desired or determined leads.

From the instrumentation amplifiers 31, the signals pass to a switching device 32, which selectively selects the lead to be analyzed. The sensed, analyzed and distributed signals are then passed to the filter block 33 and, after passing by the high pass filter 33*a*, low pass filter 33*b* and band reject filter 33*r*, the conditioned signals are sent to the receiver of the sensed ECG signal 35, ending step C of the present method.

After step C, already in step D of the method, there is the transmission of the ECG bipolar, unipolar our unipolar precordial leads by transmission means via communication protocols and telephone routes. This transmission occurs from the receiver of the sensed ECG signal 35 to the processing unit 40 and can be done via mobile or fixed telephone network, among other similar means.

After step D, the processing unit 40 transforms the leads into ECG graphs.

The advantages of the apparatus 10 for sensing and processing electrical cardiac signals and the method of remote sensing and processing of electrical cardiac signals, objects of the present invention, lie in that they may be used by laypersons with little guidance, such as with telephone guidance, for instance. Furthermore, the apparatus 10 is very practical because it does not need accessories, such as sets of wires and contact tips (hooks or alligator clips), which increases the durability of the apparatus 10. Another advantage observed is the reduction of noise and interferences in the sensing of the signal.

Having described examples of the invention with reference to its preferred embodiments, it is to be understood that the scope of the present invention embraces other possible variations, being limited solely by the appended claims, including the possible equivalents therein.

What is claimed is:

1. A method of remote sensing and processing of electrical cardiac signals of a human body by means of an apparatus for sensing and processing electrical cardiac signals, the apparatus comprising a plurality of electrical signal sensing electrodes associated with an electronic processing circuit, said method comprising the steps of:

A) obtaining three classical leads DI, DII, and DIII and three augmented leads, aVF, aVR, and aVL with a single positioning of the apparatus associated with a body surface of a frontal portion of a subject's skin at a thoracic or abdominal region so that an electrode, arranged on a single housing of the apparatus is directed to a subject's left leg and, simultaneously, contacting a first finger of the subject's hand on another electrode and a second finger of the subject's hand on still another electrode, said first and second fingers originating from different hands of the same subject;

B) positioning the apparatus' housing on three different standard body locations of the subject's thoracic region for precordial sensing;

C) sensing electrical signals originating from the subject's heart for each of standard body locations of steps A and B and transmitting these signals to the electronic processing circuit;

D) processing the electrical signals sensed by the electrical signal sensing electrodes by the electronic processing circuit and selectively transforming these electrical signals into ECG bipolar, unipolar, or unipolar precordial leads; and E) transmitting wirelessly twelve ECG bipolar, unipolar, or unipolar precordial leads to at least one processing unit, the processing unit transforming the leads into ECG graphs.

2. The method according to claim 1, wherein, in step A, the apparatus' housing for sensing and processing electrical signals is put into contact with the subject's thoracic region or abdomen.

3. The method according to claim 1, wherein, in step B, there are multiple standard body positioning of the housing.

4. The method according to claim 1, wherein, in steps A and B, other fingers of the subject's hand are positioned on an electrical ground point of the apparatus.

5. The method according to claim 1, wherein, in step C, the sensing of the subject's electrical cardiac signals occurs according to timing programmed by the electronic processing circuit.

6. The method according to claim 1, wherein, in step D, transmission of ECG bipolar, unipolar or unipolar precordial leads is done by transmission means via communication protocols and telephone routes.

* * * * *